United States Patent [19]
Adams

[11] Patent Number: 5,470,346
[45] Date of Patent: Nov. 28, 1995

[54] CONNECTOR PORTS FOR AN IMPLANTABLE DEFIBRILLATOR

[75] Inventor: Theodore P. Adams, Edina, Minn.

[73] Assignee: Angeion Corporation, Plymouth, Minn.

[21] Appl. No.: 156,984

[22] Filed: Nov. 23, 1993

Related U.S. Application Data

[63] Continuation of Ser. No. 853,052, Mar. 18, 1992, abandoned.

[51] Int. Cl.$^6$ .................................................. A61N 1/39
[52] U.S. Cl. .................................................. 607/37
[58] Field of Search ................................ 607/4, 5, 37

[56] References Cited

U.S. PATENT DOCUMENTS

| | | | |
|---|---|---|---|
| 4,499,907 | 2/1985 | Kallok et al. | 128/419 D |
| 4,548,203 | 10/1985 | Tacker, Jr. et al. | |
| 4,603,705 | 8/1986 | Speicher et al. | 128/786 |
| 4,708,145 | 11/1987 | Tacker, Jr. et al. | |
| 4,774,950 | 10/1988 | Cohen | 128/419 D |
| 4,787,389 | 11/1988 | Tarjan | 128/419 D |
| 5,163,427 | 11/1992 | Keimel | 607/5 |
| 5,306,291 | 4/1994 | Kroll et al. | 607/5 |
| 5,314,430 | 5/1994 | Bardy | 607/37 |

OTHER PUBLICATIONS

Medtronic PCD Device Tachyarrhythmia Control System System Reference Guide, Apr. 1992.
VF Therapy–Programmable Parameters, Apr. 1992.
Epicardial Implantation Procedure, Apr. 1992.
M/Sequential–Pulse, Multiple Pathway Defibrillation Method.

*Primary Examiner*—William E. Kamm
*Assistant Examiner*—Scott M. Getzow
*Attorney, Agent, or Firm*—Patterson & Keough

[57] ABSTRACT

A defibrillator having a connector utilizing a plurality of ports aligned therein to accommodate sensing leads, and positive and negative defibrillator electrode leads. The positive defibrillator leads are internally connected in common and can facilitate the use of two positive defibrillator leads. Alternative embodiments illustrate methods of having different post polarities for use in situations where having different electrode polarities is beneficial. Other alternative embodiments illustrate methods for limiting current or EMF through one of the commonly wire defibrillator ports.

7 Claims, 3 Drawing Sheets

1

CONNECTOR PORTS FOR AN IMPLANTABLE DEFIBRILLATOR

This application is a continuation of application Ser. No. 07/853,052, filed Mar. 18, 1992, now abandoned.

BACKGROUND OF THE INVENTION

1. Field of the Invention

The present invention relates to implantable defibrillators, and more specifically, pertains to a connector of the implanted device which is used to connect to the lead system.

2. Description of the Prior Art

Prior art defibrillators have ports for connecting sensing leads and ports for connection to defibrillating electrodes. FIG. 1 illustrates a side view of the prior art defibrillator 10 having a pulse generator 12 and a connector block member 14 having several pin configurations which aligns to the upper portion of the pulse generator 12.

FIG. 2 illustrates an end view of a defibrillator 10, and specifically, the connector block member 14 as viewed along line 2—2 of FIG. 1 and having a pin configuration including + sensing electrode port 16, a − sensing electrode port 18, a + defibrillation electrode port 20, and a − defibrillation electrode port 22.

FIG. 3 illustrates an end view of the defibrillator 10 and of the connector block member 14 along line 3—3 of FIG. 1, and a different pin configuration including a single port 24 for both the + and − sensing as in the case of an IS1 standard pacing lead. The connector block member 14 also includes a + defibrillator electrode port 26 and a − defibrillator electrode port 28.

If more than two defibrillating electrodes are used, a junction box 30, commonly called a Y-adapter, is used to add a third + electrode lead 32 as illustrated in FIG. 4. This additional hardware contributes unnecessary bulk to the implant system in addition to compromising the system reliability.

The present invention overcomes the deficiencies of the prior art by providing a connector for attachment of required leads and electrodes including two positive ports, thus eliminating the requirement for a junction box 30.

SUMMARY OF THE INVENTION

The general purpose of the present invention is to provide a defibrillator connector having multiple defibrillator electrode ports, thus eliminating bulk adapters, and the need for an intervening junction box or adapters.

According to one of the preferred embodiments of the present invention, there is provided a defibrillator including a pulse generator, a connector block aligned to the top portion of the pulse generator and four or more electrical connection ports in the connector block including at least two defibrillator electrode ports connected in common, a defibrillator electrode port and an in line IS1 pacing connector port.

In one of the preferred embodiments, the common electrodes comprise the + defibrillator electrodes. A first alternative configuration have the − defibrillator electrodes in common. A second alternative embodiment features programmable polarity so that either the + or − defibrillating electrodes can share the dual ports.

2

One significant aspect and feature of the present invention is a defibrillator having more than one + defibrillation port.

Another significant aspect and feature of the present invention is a connector having more than one + defibrillator electrode port, a − defibrillator electrode port, and a IS1 in-line pacing port used for sensing leads.

Another significant aspect and feature of the present invention is the elimination of the junction box when more than one + defibrillator lead is used.

Having thus described one embodiment of the present invention, it is the principal object hereof to provide a defibrillator with a new connector with a plurality of ports.

One object of the present invention is to provide a defibrillator with at least two positive ports.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PRIOR ART

Figure 1:
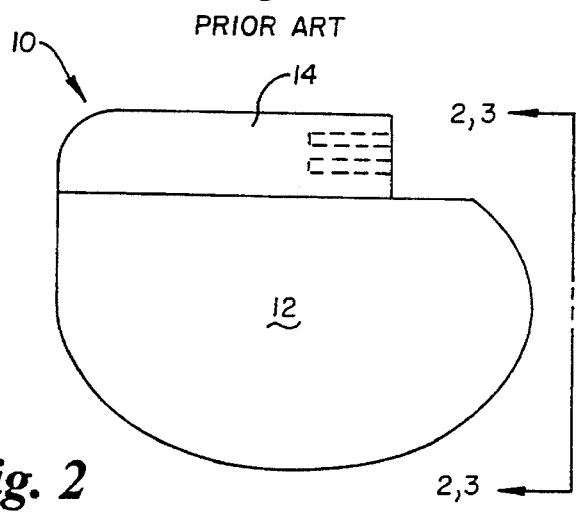
FIG. 1 illustrates a side view of a prior art defibrillator.

FIG. 1 illustrates a side view of the prior art defibrillator 10 having a pulse generator 12 and a connector block member 14 aligned to the top portion of the pulse generator 12 where all numerals correspond to those elements previously described.

Figure 2:
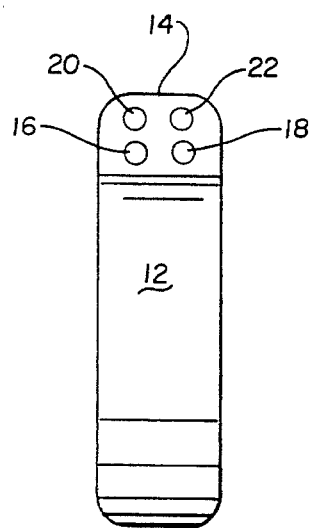
FIG. 2 illustrates an end view of the prior art defibrillator post configuration from viewing vantage 2—2.

FIG. 2 illustrates an end view of the prior art defibrillator 10 showing a first port configuration where various ports mount and secure into the connector block member 14, including a + sensing electrode port 16, a − sensing electrode port 18, a + defibrillation electrode port 20 and a − defibrillation electrode port 22.

Figure 3:
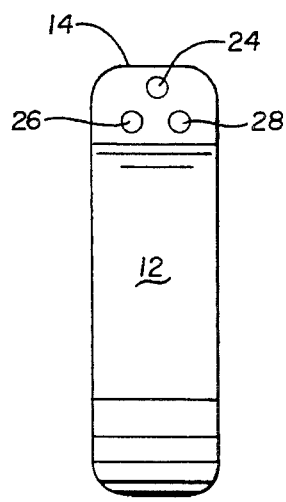
FIG. 3 illustrates an end view of the prior art defibrillator port configuration from viewing vantage 3—3.

FIG. 3 illustrates an end view of the prior art defibrillator 10 showing a second port configuration where various ports mount and secure into the connector block member 14 including a + defibrillator port 26, a − defibrillator port 28, and an IS1 in-line placing port 24 where all numerals correspond to those elements previously described.

Figure 4:
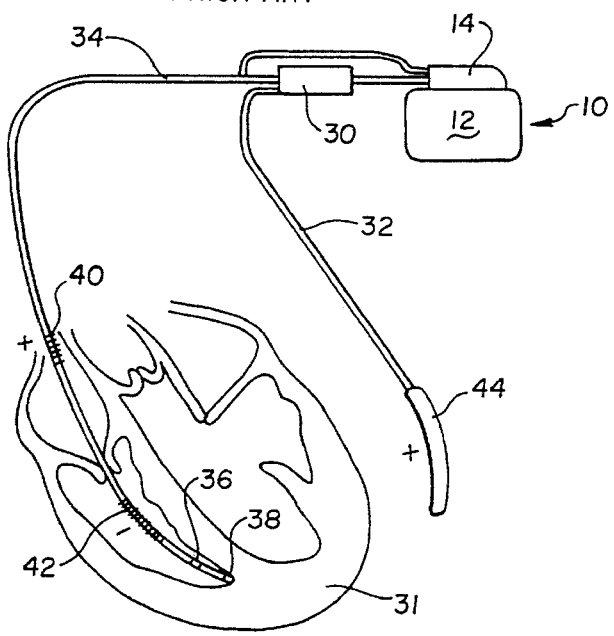
FIG. 4 illustrates a prior art defibrillator connected through a junction box to the heart.

FIG. 4 illustrates the prior art defibrillator 10 connected through a junction box 30 to a human heart 31, including lead cable 34 connected to sensing electrodes 36 and 38, + defibrillator electrode 40, − defibrillator electrode 42 and a + electrode lead 32 leading to + defibrillator electrode 44 where all other numerals correspond to those elements previously described.

DETAILED DESCRIPTION OF THE PREFERRED EMBODIMENTS

Figure 5:
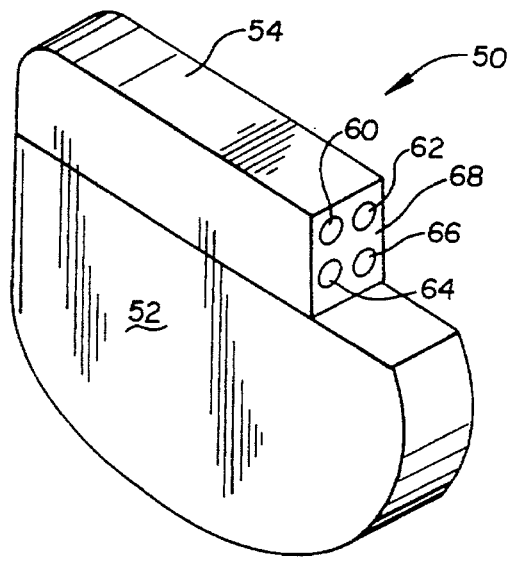
FIG. 5 illustrates a perspective view of a defibrillator with a new connection ports, the present invention.

FIG. 5 illustrates a preferred embodiment in perspective of a defibrillator 50, the present invention, having a pulse generator 52 and a connector block member 54. Connector ports 60, 62, 64 and 66 mount in the end 68 of the connector block member 54. Connector ports 60 and 62 are + defibrillator ports connected in common with each other, connector port 64 is a − defibrillator port and connector port 66 is an IS1 in-line pacing port. This arrangement allows the leads to be plugged directly into the connector block member 54 without the use of a junction box 30.

Figure 6:
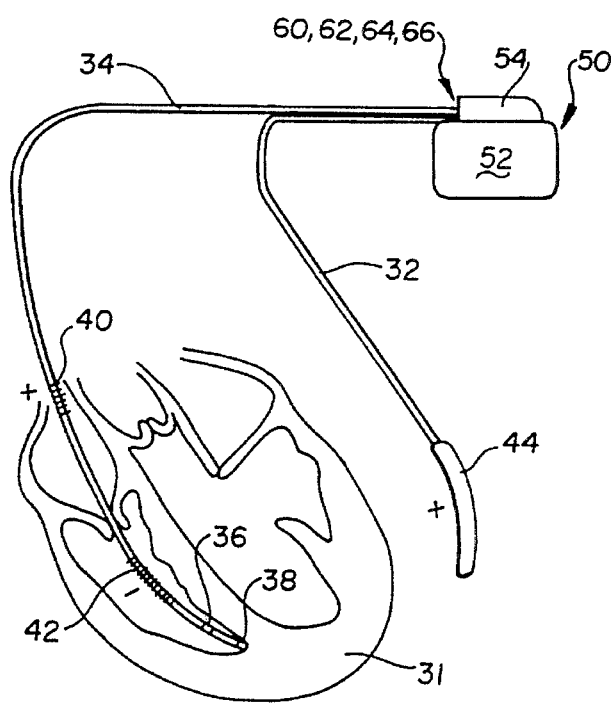
FIG. 6 illustrates a defibrillator connected to the heart.

FIG. 6 illustrates the defibrillator 50 connected to the human heart 31 by a lead cable 34 having three physically separate terminal connectors, one of which is an inline IS1 pacing connector, each of which appropriately connects to the sensing electrodes 36 and 38, the + defibrillator electrode 40, and the − defibrillator electrode 42. As in FIG. 4, a + electrode lead 32 leads to a + defibrillator electrode 44; however, unlike FIG. 4, + electrode lead 32 is directly connected to defibrillator 50, and not to junction box 30 which is absent from the present invention. All other numerals correspond to those elements previously described.

MODE OF OPERATION

FIGS. 7–11 illustrate basic circuit schematics for the polarity configuration with respect to the defibrillation electrode ports and an implantable cardioverter defibrillator (ICD) circuit 100 capable of generating a truncated capacitive-discharge countershock to be delivered to a human patient.

Figure 7:
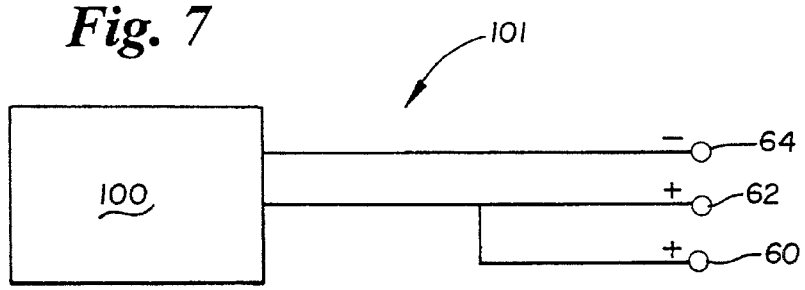
FIG. 7 illustrates an electrical circuit for the defibrillator.

FIG. 7 illustrates the preferred embodiment circuit 101 where all numerals correspond to those elements previously described. The positive defibrillator ports 60 and 62 are connected in common to the ICD circuit 100 for use of two positive defibrillator electrodes. The polarity of defibrillator port 64 is negative.

Figure 8:
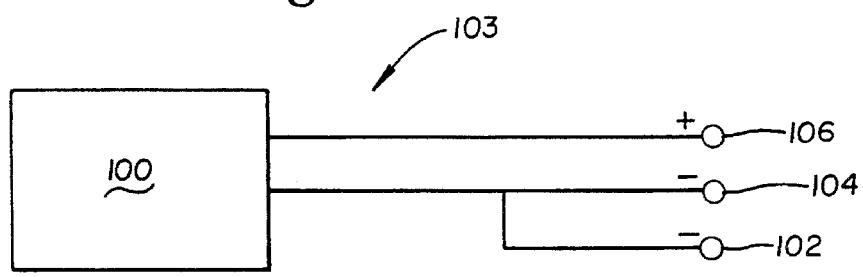
FIG. 8 illustrates a first alternative embodiment circuit for the defibrillator.

FIG. 8, a first alternative embodiment, illustrates a circuit 103 where negative defibrillator connector ports 102 and 104 are connected in common to the ICD circuit 100 for the use of two negative defibrillator electrodes. The polarity of the defibrillator port 106 is positive.

Figure 9:
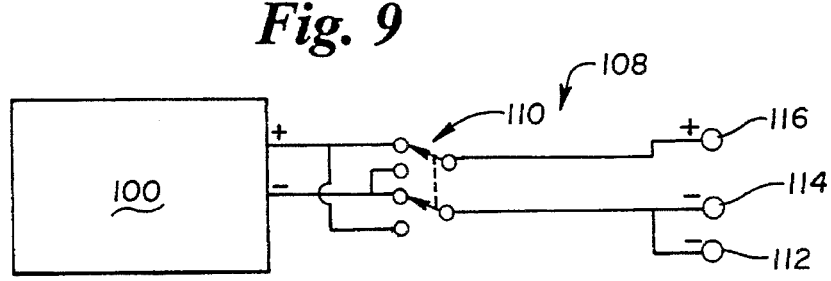
FIG. 9 illustrates a second alternative embodiment circuit for the defibrillator.

FIG. 9, a second alternative embodiment, illustrates a circuit 108 where programmable switching indicated by switch 110 allows the defibrillator ports 112, 114 and 116 to assume opposite polarities. With the switch 110 positioned as illustrated, the defibrillator ports 112 and 114 assume a − polarity and the defibrillator port 116 assumes a + polarity. Actuating the switch 110 to the opposite position allows the defibrillator ports 112 and 114 to have + polarity and the defibrillator port 116 to have − polarity.

Figure 10:
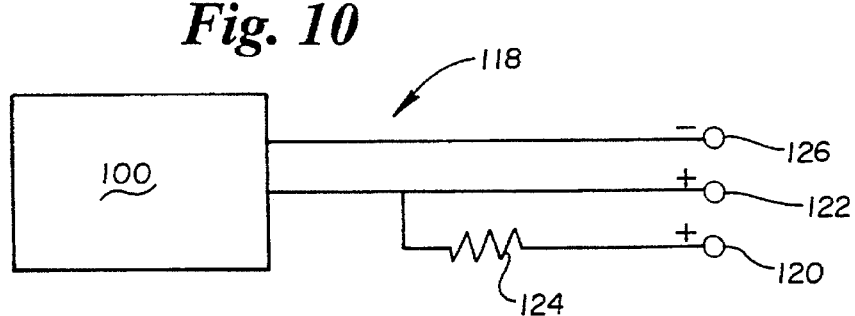
FIG. 10 illustrates a third alternative embodiment circuit for the defibrillator; and, FIG. 11 illustrates a fourth alternative embodiment circuit for the defibrillator.

FIG. 10, a third alternative embodiment, illustrates a circuit 118 where the positive defibrillator ports 120 and 122 are connected in common to the ICD circuit 100, but have a series resistor 124 between the + defibrillator port 120 and the ICD circuit 100 in order to preferentially direct more current to one electrode port than the other. The + defibrillator port 122 exhibits a low z and the + defibrillator port 120 exhibits a high z. The polarity of the defibrillator port 126 is negative.

Figure 11:
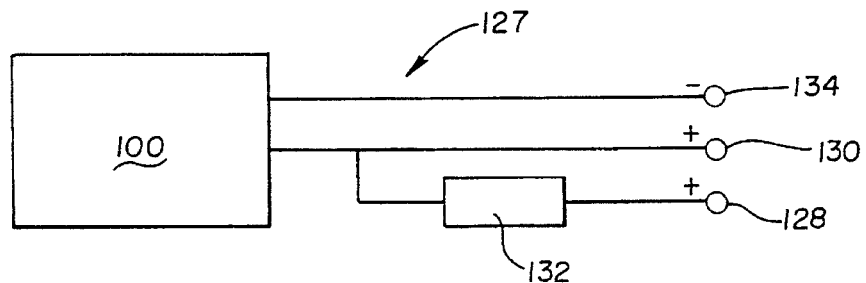

FIG. 11, a fourth alternative embodiment, illustrates a circuit 127 where the positive defibrillator ports are connected in common to the ICD circuits, but having a current limiting transistor or other current limiting device between the + defibrillator port 128 and the ICD circuit 100 to limit current through the + defibrillator port 128, while allowing a higher current to pass through the + defibrillator port 130. The polarity of the defibrillator port 134 is negative.

Various modifications can be made to the present invention without departing from the apparent scope hereof.

I claim:

1. An implantable defibrillator for delivering a defibrillation countershock to at least three implantable defibrillator electrodes adapted for implantation within a human patient, the defibrillator comprising:

a. an implantable housing including circuit means for generating a truncated capacitive-discharge of greater than about 0.5 joules as the defibrillation countershock;

b. a connector block member in said housing having at least four terminal ports;

c. at least three of said terminal ports in said connector block member being defibrillator terminal ports electrically connected to said circuit means and each of said defibrillator terminal ports being electrically connected to a unique one of at least three implantable defibrillation electrodes;

d. at least one of said terminal ports being a sensing terminal port electrical connected to said circuit means and to an implantable sensing electrode; and e. at least two of said defibrillator terminal ports having a same polarity, such that said implantable defibrillator does not require the use of an implantable junction box in order to deliver the countershock to said at least three defibrillator electrodes electrically connected to said defibrillator terminal ports.

2. The defibrillator according to claim 1 wherein said at least two defibrillator terminal ports having the same polarity include at least two positive terminal ports.

3. The defibrillator according to claim 1 wherein said at least two defibrillator terminal vorts having the same polarity include at least two negative terminal ports.

4. The defibrillator according to claim 1 further including: programmable switch means electrically connected between said defibrillator terminal ports and said circuit for selectively determining which of at least two of said defibrillator terminal ports will have the same polarity.

5. The defibrillator according to claim 1 further including:
   resistor means electrically connected between said defibrillator terminal ports and said circuit for selectively directing more current of said countershock to one or more of said defibrillator terminal ports.

6. The defibrillator according to claim 1 further including:
   current limiting means electrically connected between said defibrillator terminal ports and said circuit for selectively directing less current of said countershock to one or more of said defibrillator terminal ports.

7. The defibrillator according to claim 1 wherein said implantable housing comprises one of said at least three defibrillator electrodes.

* * * * *